United States Patent
Boldingh et al.

(10) Patent No.: US 6,359,185 B1
(45) Date of Patent: *Mar. 19, 2002

(54) SELECTIVE AROMATICS DISPROPORTIONATION PROCESS

(75) Inventors: Edwin P. Boldingh, Arlington Heights; Jennifer S. Holmgren, Bloomingdale; Gregory J. Gajda, Mount Prospect; Michael H. Quick, Arlingotn Heights, all of IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/594,674

(22) Filed: Jun. 16, 2000

Related U.S. Application Data

(63) Continuation-in-part of application No. 09/218,320, filed on Dec. 22, 1998, now abandoned, and a continuation-in-part of application No. 08/987,194, filed on Dec. 8, 1997, now abandoned, said application No. 09/218,320, is a continuation-in-part of application No. 08/986,622, filed on Dec. 8, 1997, now abandoned.

(51) Int. Cl.[7] .......................... C07C 5/52; B01J 27/182
(52) U.S. Cl. ........................ 585/475; 585/470; 502/214
(58) Field of Search ................. 585/475, 470; 502/214, 208, 60, 64, 67, 77; 525/10, 32.2

(56) References Cited

U.S. PATENT DOCUMENTS

| | | | | |
|---|---|---|---|---|
| 4,011,276 A | * | 3/1977 | Chu ........................ 260/672 T |
| 4,016,219 A | | 4/1977 | Kaeding ....................... 585/471 |
| 4,097,543 A | * | 6/1978 | Haag et al. ............... 260/672 T |
| 4,182,923 A | * | 1/1980 | Chu ........................... 585/475 |
| 4,537,866 A | * | 8/1985 | Gilson ......................... 502/70 |
| 4,629,717 A | | 12/1986 | Chao .......................... 502/208 |
| 4,724,066 A | | 2/1988 | Kirker et al. ............... 208/114 |
| 5,169,812 A | | 12/1992 | Kocal et al. .................. 502/61 |
| 6,008,423 A | * | 12/1999 | Holmgren et al. .......... 585/475 |
| 6,063,977 A | * | 5/2000 | Gajda et al. ................ 585/475 |
| 6,114,592 A | * | 9/2000 | Gajda et al. ................ 585/475 |
| 6,191,331 B1 | * | 2/2001 | Boldingh .................... 585/475 |

* cited by examiner

Primary Examiner—Thuan D. Dang
(74) Attorney, Agent, or Firm—John G. Tolomei; John F. Spears, Jr.

(57) ABSTRACT

An improved process is disclosed for the selective disproportionation of toluene. The process uses a zeolitic catalyst which is oil-dropped in an amorphous aluminum phosphate binder and optionally is selectively precoked prior to toluene disproportionation. The catalyst and process provide enhanced selectivity for the production of paraxylene.

13 Claims, 5 Drawing Sheets

SELECTIVE AROMATICS DISPROPORTIONATION PROCESS

CROSS-REFERENCE TO RELATED APPLICATION

This application is a continuation-in-part of prior application 09/218,320 filed Dec. 22, 1998, now abandoned which application was a continuation-in-part of Ser. No. 08/986,622, filed Dec. 8, 1997, now abandoned and a continuation-in-part of prior application Ser. No. 08/987,194, filed Dec. 8, 1997, now abandoned the contents of all being incorporated herein by reference.

BACKGROUND OF THE INVENTION

This invention relates to an improved process for the conversion of aromatic hydrocarbons. More specifically, the invention concerns disproportionation and transalkylation of aromatic hydrocarbons to obtain xylenes through the use of a zeolitic catalyst.

The xylene isomers are produced in large volumes from petroleum as feedstocks for a variety of important industrial chemicals. The most important of the xylene isomers is paraxylene, the principal feedstock for polyester which continues to enjoy a high growth rate from large base demand. Orthoxylene is used to produce phthalic anhydride, which has high-volume but mature markets. Metaxylene is used in lesser but growing volumes for such products as plasticizers, azo dyes and wood preservers. Ethylbenzene generally is present in xylene mixtures and is occasionally recovered for styrene production, but usually is considered a less-desirable component of $C_8$ aromatics.

Among the aromatic hydrocarbons, the overall importance of the xylenes rivals that of benzene as a feedstock for industrial chemicals. Neither the xylenes nor benzene are produced from petroleum by the reforming of naphtha in sufficient volume to meet demand, and conversion of other hydrocarbons is necessary to increase the yield of xylenes and benzene. Most commonly, toluene is dealkylated to produce benzene or disproportionated to yield benzene and $C_8$ aromatics from which the individual xylene isomers are recovered. More recently, processes have been introduced to disproportionate toluene selectively to obtain higher-than-equilibrium yields of paraxylene.

A current objective of many aromatics complexes is to increase the yield of xylenes and to de-emphasize benzene production. Demand is growing faster for xylene derivatives than for benzene derivatives. Refinery modifications are being effected to reduce the benzene content of gasoline in industrialized countries, which will increase the supply of benzene available to meet demand. Benzene produced from disproportionation processes often is not sufficiently pure to be competitive in the market. A higher yield of xylenes at the expense of benzene thus is a favorable objective, and processes to transalkylate $C_9$ aromatics along with toluene have been commercialized to obtain high xylene yields.

U.S. Pat. No. 4,016,219 (Kaeding) discloses a process for toluene disproportionation using a catalyst comprising a zeolite which has been modified by the addition of phosphorus in an amount of at least 0.5 mass-%. The crystals of the zeolite are contacted with a phosphorus compound to effect reaction of the zeolite and phosphorus compound. The modified zeolite then may be incorporated into indicated matrix materials.

U.S. Pat. No. 4,097,543 (Haag et al.) teaches toluene disproportionation for the selective production of paraxylene using a zeolite which has undergone controlled precoking. The zeolite may be ion-exchanged with a variety of elements from Group IB to VIII, and composited with a variety of clays and other porous matrix materials.

U.S. Pat. No. 4,629,717 (Chao) discloses a phosphorus-modified alumina hydrogel formed by gelation of a homogeneous hydrosol. The composite has a relatively high surface area of 140–450 $m^2/g$ and high activity and selectivity in 1-heptene conversion tests.

U.S. Pat. No. 4,724,066 (Kirker et al.) teaches a hydrocarbon dewaxing process using a catalyst comprising a zeolite and a crystalline aluminum phosphate; aside from the differences in process, Kirker differs from the present invention in specifying a crystalline rather than amorphous aluminum phosphate component.

U.S. Pat. No. 5,169,812 (Kocal et al.) teaches a catalyst for aromatization of light hydrocarbons comprising a zeolite, preferably ZSM-5, a gallium component and an aluminum phosphate binder. The composite is treated with a weakly acidic solution, dried and calcined to increase its tolerance to hydrogen at high temperatures.

U.S. Pat. No. 4,011,276 (Chu) presents a process for the disproportionation of toluene using a catalyst comprising a crystalline aluminosilicate zeolite such as MFI which has been modified by the addition of oxides of phosphorous and magnesium.

U.S. Pat. No. 4,182,923 (Chu) teaches a high conversion process to disproportionate toluene to benzene and xylenes rich in para-xylene. The process employs a crystalline aluminosilicate zeolite such as MFI which has been modified by treatment with ammonium hydrogen phosphate to deposit at least 0.5 weight percent phosphorous.

Workers in the field of aromatics disproportionation continue to seek processes and catalysts having exceptionally high selectivity for paraxylene from toluene combined with favorable activity and stability.

SUMMARY OF THE INVENTION

It is an object of the present invention to provide an improved process for the disproportionation of aromatic hydrocarbons to yield desirable alkylaromatic isomers. A specific objective is to obtain a high yield of paraxylene by disproportionation of toluene.

This invention is based on the discovery that high activity with potential for selectivity to paraxylene is obtained by disproportionation of toluene using a zeolitic catalyst which has been oil-dropped with an amorphous aluminum phosphate binder.

The present invention therefore is directed to a process for the disproportionation of a toluene feedstock to obtain a product comprising paraxylene using an oil-dropped spherical catalyst comprising a zeolitic aluminosilicate having a pore diameter of from about 5 to 8 Å and an amorphous aluminum phosphate binder. The catalyst optionally has an enhanced surface silicon content. Preferably the product contains paraxylene in excess of its equilibrium concentration at disproportionation conditions. The preferred catalyst of the present invention comprises a zeolitic aluminosilicate preferably selected from MFI, MEL and MTW, and most preferably comprises MFI. In one embodiment, the catalyst has a particle size of no more than about 1 mm.

The catalyst preferably is subjected to a precoking step prior to its use for disproportionation/transalkylation in order to deposit a controlled concentration of carbon on the catalyst and increase its selectivity to paraxylene in the product.

A process combination optionally comprises a xylene-separation zone; preferably, paraxylene is recovered by adsorption or a combination of adsorption and crystallization.

These as well as other objects and embodiments will become apparent from the detailed description of the invention.

DESCRIPTION OF THE PREFERRED EMBODIMENTS

Figure 1:
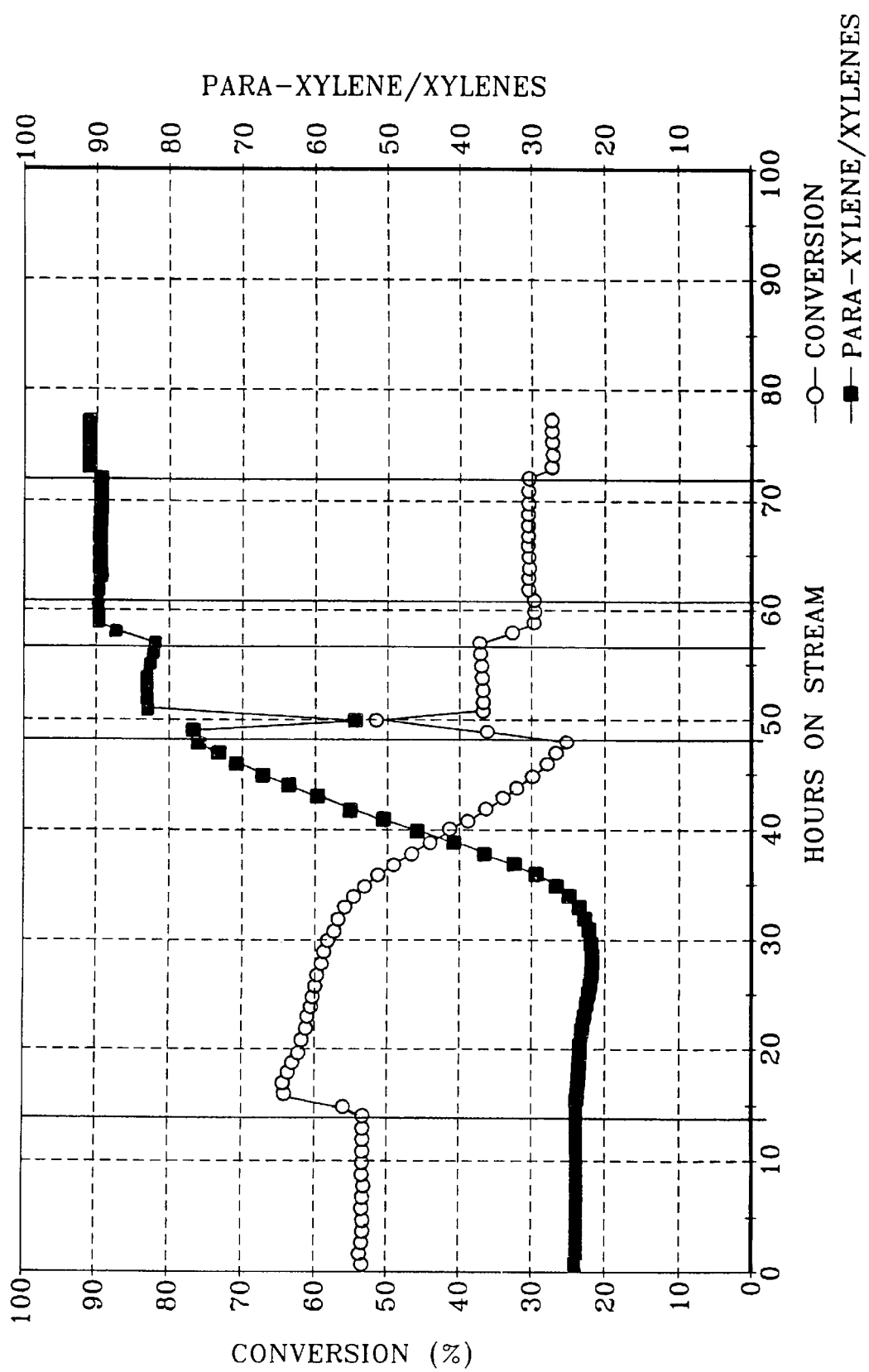
FIG. 1 shows conversion and selectivity in a pilot-plant toluene-disproportionation test.

An embodiment of the present invention therefore is directed to the disproportionation of a toluene feedstock to obtain a product comprising paraxylene using an oil-dropped spherical catalyst comprising a substantially phosphorous free zeolitic aluminosilicate having a pore diameter of from about 5 to 8 Å and an amorphous aluminum phosphate binder. The binder preferably has an Al to P atomic ratio of about 1:1 to about 5:1. The paraxylene content of the product preferably is in excess of its equilibrium concentration at disproportionation conditions. Other embodiments of the invention encompass but are not limited to parameters such as incremental and alternative feedstocks, catalyst composition, catalyst conditioning for paraxylene selectivity and operating conditions.

Broadly, the feedstock to the subject process comprises substantially pure aromatic hydrocarbons derived from one or more sources. Aromatics may be produced synthetically, for example, from naphtha by catalytic reforming or by pyrolysis followed by hydrotreating to yield an aromatics-rich product. The aromatics feedstock may be derived from such product with suitable purity by extraction of aromatic hydrocarbons from a mixture of aromatic and nonaromatic hydrocarbons and fractionation of the extract. Large quantities of aromatic hydrocarbons are recovered commercially in this manner. For instance, aromatics may be recovered from a reformate through the use of a selective solvent, such as one of the sulfolane type, in a liquid-liquid extraction zone. When the severity of reforming or pyrolysis is sufficiently high, extraction may be unnecessary and fractionation may be sufficient to prepare the feedstock which should contain no more than about 10 mass-% and preferably less than about 1 mass-% nonaromatics. The recovered aromatics may then be separated into streams having the desired carbon number range by fractionation. The aromatic hydrocarbons may comprise one or more of toluene, xylene isomers, ethylbenzene, or $C_9$ and heavier aromatics. A preferred toluene feedstock prepared in this manner usually is fractionated to separate benzene and $C_8$ aromatics, and the degree of fractionation may be adjusted in accordance with economic factors of the disproportionation process.

The toluene feedstock, usually in admixture with toluene recycled from the products of the disproportionation reaction, is preferably admixed with free hydrogen to effect a combined feed to a disproportionation zone. If present, the hydrogen need not exceed a 20:1 mole ratio to feedstock hydrocarbons to effect satisfactory stability in the disproportionation reaction, and preferably is in the range of from about 0.5 to 10 mole ratio. The hydrogen may contain hydrocarbons, such as methane and ethane, and inerts such as nitrogen, but preferably is in a concentration of at least about 90 mole-% to avoid large hydrogen losses and unfavorable process economics. The disproportionation reaction yields a paraxylene-containing product which usually also comprises benzene, other $C_8$ aromatics, and smaller amounts of $C_9+$ aromatics.

The combined feed to the disproportionation zone usually is first heated by indirect heat exchange against the effluent of the reaction zone and is then further heated in a fired heater. The vaporous stream is then passed through a reaction zone which may comprise one or more individual reactors. The use of a single reaction vessel having a fixed cylindrical bed of catalyst is preferred, but other reaction configurations utilizing moving beds of catalyst or radial-flow reactors may be employed if desired. Passage of the combined feed through the reaction zone effects the production of a vaporous effluent stream comprising hydrogen and both the feed and product hydrocarbons. This effluent is normally cooled by indirect heat exchange against the stream entering the reaction zone and then further cooled through the use of air or cooling water. The temperature of the effluent stream is normally lowered sufficiently to effect the condensation of substantially all of the feed and product hydrocarbons having six or more carbon atoms per molecule. The resultant mixed-phase stream is passed into a vapor-liquid separator wherein the two phases are separated and from which the hydrogen-rich vapor is recycled to the reaction zone. The condensate from the separator is passed into a stripping column in which substantially all $C_5$ and lighter hydrocarbons present in the effluent are concentrated into an overhead stream and removed from the process. An aromatics-rich stream is recovered as net stripper bottoms which is referred to herein as the disproportionation effluent stream.

The catalyst preferably is subjected to precoking as described hereinbelow to increase the proportion of paraxylene in the $C_8$ aromatics product above equilibrium levels at disproportionation conditions.

Conditions employed in the disproportionation zone of the subject process normally include a temperature of from about 200° to 600° C., and preferably from about 350° to 575° C. The temperature required to maintain the desired degree of conversion will increase as the catalyst gradually loses activity during processing. Normal end-of-run temperatures may therefore exceed start-of-run temperatures by 65° C. or more. In the transalkylation embodiment wherein toluene and $C_9$ aromatics are present in the combined feed, reaction temperatures generally are somewhat lower within the range of about 200° to 525° C.

The disproportionation zone is operated at moderately elevated pressures broadly ranging from about 100 kPa to 6 MPa absolute. A preferred pressure range is from 2 to 3.5 MPa. The disproportionation reaction can be effected over a wide range of space velocities, with higher space velocities effecting a higher ratio of paraxylene at the expense of conversion. Liquid hourly space velocities generally are the range of from about 0.2 to 10 $hr^{-1}$, with a value in the range of from 0.8 to 3 $hr^{-1}$ being preferred.

It is within the scope of the invention that the feedstock comprises a heavy-aromatics stream comprising $C_9$ aromatics as a component of the feed to the present process. Transalkylation of toluene and $C_9$ aromatics is effected thereby within the disproportionation conditions described above. The heavy-aromatics stream may be derived from the same or a different refinery or petrochemical process as the toluene feedstock and/or may be recycled from the separation of the product of the subject disproportionation/transalkylation process. Benzene also may be present in the combined feed to the subject disproportionation/transalkylation process. However, it is preferred that the feedstock consists essentially of toluene in order to effect a high degree of paraxylene selectivity as described hereinbelow.

The disproportionation reaction zone effluent stream is separated into a light recycle stream, a paraxylene-containing mixed-$C_8$-aromatics product and a heavy-aromatics stream. The paraxylene-containing product may be sent to a xylene separation zone for recovery of pure paraxylene; optionally, other xylenes and ethylbenzene also may be recovered as pure products. The paraxylene-containing stream preferably contains paraxylene in proportion to total xylenes, in excess of its equilibrium concentration at disproportionation conditions, more preferably at least about 80 mass-% paraxylene, and most preferably at least about 85 mass-% paraxylene. The light recycle stream may be diverted to other uses such as to benzene and toluene recovery, but preferably is partially recycled to the disproportionation zone since it contains not only benzene and toluene but also amounts of nonaromatics which would remain with the benzene and reduce its commercial value. The heavy recycle stream contains substantially all of the $C_9$ and heavier aromatics and may be either withdrawn as a product of the process or partially or totally recycled to the reaction if transalkylation is an objective of the process.

The xylene-separation zone may utilize one or more different separation techniques such as fractionation, crystallization or selective adsorption to recover pure paraxylene from the paraxylene-containing stream in the xylene-separation zone. Conventional crystallization is disclosed in U.S. Pat. No. 3,177,255, U.S. Pat. No. 3,467,724 and U.S. Pat. No. 3,662,013. Various other crystallization alternatives are discussed in U.S. Pat. No. 5,329,061 and U.S. Pat. No. 6,060,634, incorporated by reference. In an embodiment in which the paraxylene-containing product has a paraxylene content substantially in excess of the equilibrium concentration, recovery of pure paraxylene may be effected using only a single stage of crystallization corresponding to the higher-temperature purification stage of conventional crystallization.

An alternative adsorptive separation zone comprises a bed of molecular sieves operated in accordance with the teaching of U.S. Pat. No. 3,201,491 to simulate the use of a continuously moving bed of molecular sieves. Subsequent improvements to the process are described in U.S. Pat. No. 3,696,107 and U.S. Pat. No. 3,626,020. Details on the operation of the xylene-separation zone may also be obtained from U.S. Pat. No. 4,039,599 and U.S. Pat. No. 4,184,943. The simulated cocurrent adsorptive separation process of U.S. Pat. No. 4,402,832 may be employed. The extract and raffinate streams may be handled as described in these references or as described in U.S. Pat. No. 4,381,419.

The skilled routineer will recognize variations in the process combination described above which are within the scope of the invention. For example, benzene as well as toluene may be charged to the disproportionation zone as a supplementary feedstock. The xylene-separation zone may use one or more of several known separation techniques such as adsorption, crystallization and fractionation such as the combined adsorption and crystallization process described in previously cited U.S. Pat. No. 6,060,634 or in U.S. Pat. No. 5,284,992. Orthoxylene and/or metaxylene may be recovered as pure products from the xylene-separation zone. The recovered xylenes are then used primarily as raw materials to produce a variety of other organic compounds such as plastics. A high percentage of the world's paraxylene production is converted into polyester fiber by oxidation to terephthalic acid followed by reaction with ethylene glycol using one of several competing commercial technologies.

The catalyst of the present invention comprises a molecular sieve and a refractory inorganic oxide. The preferred molecular sieves are zeolitic aluminosilicates which may be any of those which have a $Si:Al_2$ ratio greater than about 10, preferably greater than 20, and a pore diameter of about 5 to 8 Angstroms (Å). Specific examples of zeolites which can be used are the MFI, MEL, EUO, FER, MFS, MTT, MTW, TON, MOR and FAU types of zeolites. Pentasil zeolites MFI, MEL, MTW and TON are preferred, and MFI-type zeolites, often designated ZSM-5, are especially preferred.

The preparation of the preferred MFI-type zeolites is well known in the art. The zeolites generally are prepared by crystallizing a mixture containing an alumina source, a silica source, an alkali metal source, water and an alkyl ammonium compound or its precursor. The amount of zeolite present in the catalyst can vary considerably but usually is present in an amount from about 30 to 90 mass percent and preferably from about 50 to 80 mass percent of the catalyst.

In an optional embodiment the zeolite is treated to increase its performance. Preferably this is via a surface treatment. In one such treatment, the zeolite is contacted with a dilute acid solution or an aqueous solution of a weakly acidic ammonium salt preferably prior to being composited with a binder. The concentration of these salts can vary from about 0.1 to about 5 molar. The acids which can be used include hydrochloric, acetic, nitric, and sulfuric acid.

Although concentrated acids could be used, they would degrade the zeolite and the integrity of the particles as well as removing the undesirable aluminum species. Thus, it is desirable to use dilute acids which have a molarity from about 0.1 to about 5 moles/liter. The ammonium salts which can be used include ammonium chloride, ammonium acetate and ammonium nitrate. Of these treatment solutions, it is preferred to use a sulfuric acid solution.

The treating solution is contacted with the dried catalyst particles at a temperature of about 50° to about 100° C. for a time of about 1 to about 48 hours. After this treatment, the particles are separated from the aqueous solution, dried and calcined at a temperature of about 500° to about 700° C. for a time of about 1 to about 15 hours, thereby providing the catalyst of the instant invention.

In an alternative embodiment, the catalyst particles comprising a zeolite and an amorphous aluminum phosphate binder are treated with the dilute acid solution or aqueous solution of a weakly acidic ammonium salt at conditions as described hereinabove. When treating the bound zeolite, an ammonium nitrate treating solution is preferred.

The purpose of treating the zeolite with one of the solutions described above is to remove acid sites which effect isomerization, dealkylation or ring loss of aromatic compounds during disproportionation. The exact nature of the species which is removed by this treatment step is not known. Without wishing to be bound by a particular theory, it is postulated that the deleterious sites which are removed comprise aluminum species.

Pursuant to treatment of the unbound or bound zeolite, therefore, the proportion of silicon at the surface of the zeolite is higher than that of the untreated zeolite. Preferably the silicon/aluminum ratio, expressed as $Si/Al_2$, is increased by about 5 or more at the surface of the zeolite and more preferably by at least 10 relative to the ratio in the untreated zeolite. The "surface" is defined for purposes of the present invention as a layer at the external surface of the zeolite which is less than about 100 angstroms in depth, usually about 50 angstroms or less in depth, and more usually about 10 angstroms or less in depth.

Elemental surface analysis to assess component ratios is effected by any suitable method as taught in the art, e.g., XPS, Auger spectroscopy or SIMS. XPS, or x-ray photoelectron spectroscopy, is a standard analytical technique which indicates the composition of a surface layer about 1 to 10 nm deep, more usually up to about 5 nm deep, as well as the binding energy of each type of atom. XPS is particularly effective in determining surface ratios of framework components. The surface ratios are compared before and after treating to determine the degree of enrichment of silicon in the surface of the zeolite.

While these treatments may change the surface composition of the zeolite they are not intended to introduce new compounds or elements into the zeolite. The zeolite therefore preferably only comprises the atoms forming its framework, charge balancing cations and other atoms resulting from manufacturing, as opposed to post-manufacturing treatment steps. It is specifically preferred that the zeolite is substantially free of moderators such as phosphorous which might possibly be present on its surface as from contact with the binder. As large scale production is normally performed in plants producing a variety of materials, some contamination may occur. The term "substantially free" and its equivalents is therefore intended to indicate a concentration less than about 0.15 wt. percent of the indicated element.

Zeolitic catalysts usually comprise a binder material as the raw zeolite powder may be a light material unsuitable for use in a high flow rate fixed bed reactor. Bound catalysts have good particle strength and other benefits. A preferred binder or matrix component is a nonacidic homogeneous material prepared by "oil dropping" a mixture containing phosphorous and an alumina sol to produce a material referred to herein as aluminum phosphate. This is a uniform chemical material dissimilar from those made by simply impregnating an alumina with a phosphorous compound. For instance, oil-dropped materials normally have a unique pore size and volume distribution. Phosphorus may alternatively be incorporated with the alumina prior to contacting the zeolite by other acceptable methods which produce equivalent materials. The zeolite and binder are mixed and formed into particles by means well known in the art such as gellation, pilling, nodulizing, marumerizing, spray drying, extrusion or any combination of these techniques. The preferred method of preparing the zeolite/aluminum phosphate composite involves adding the zeolite to an alumina sol containing a phosphorus compound, forming the resultant alumina-phosphorous sol/zeolite mixture into particles by employing the oil-drop method described hereinbelow, and calcining the spherical particles. This method is not believed to result in the substantial incorporation of phosphorous into the structure or pores of the zeolite. Some incidental combination or possibly reaction may occur at the surface of the zeolite particles, but the bulk of the zeolite remains untreated and substantially free of phosphorous.

The oil-drop method of preparing the aluminum phosphate is described in U.S. Pat. No. 4,629,717 which is incorporated by reference. The technique described in the '717 patent involves the gellation of a hydrosol of alumina which contains a phosphorus compound using the well-known oil-drop method. Generally this technique involves preparing a hydrosol by digesting aluminum in aqueous hydrochloric acid at reflux temperatures of about 80° to 105° C. The ratio of aluminum to chloride in the sol ranges from about 0.7:1 to 1.5:1 mass ratio. A phosphorus compound is now added to the sol. Preferred phosphorus compounds are phosphoric acid, phosphorous acid and ammonium phosphate. The relative amount of phosphorus and aluminum expressed in molar ratios ranges from about 10:1 to 1:100, respectively, on an elemental basis. The zeolite is added to the aluminum phosphate hydrosol and the mixture is gelled. One method of gelling this mixture involves combining a gelling agent with the mixture and then dispersing the resultant combined mixture into an oil bath or tower which has been heated to elevated temperatures such that gellation occurs with the formation of spheroidal particles. The gelling agents which may be used in this process are hexamethylene tetraamine, urea or mixtures thereof. The gelling agents release ammonia at the elevated temperatures which sets or converts the hydrosol spheres into hydrogel spheres. The spheres are then continuously withdrawn from the oil bath and typically subjected to specific aging and drying treatments in oil and in ammoniacal solution to further improve their physical characteristics. The resulting aged and gelled particles are then washed and dried at a relatively low temperature of about 100° to 150° C. and subjected to a calcination procedure at a temperature of about 450° to 700° C. for a period of about 1 to 20 hours. The amount of phosphorus-containing alumina component present (as the oxide) in the catalyst can range from about 10 to 70 mass percent and preferably from about 20 to 50 mass percent.

The combined mixture preferably is dispersed into the oil bath in the form of droplets from a nozzle, orifice or rotating disk. Alternatively, the particles may be formed by spray-drying of the mixture at a temperature of from about 425° to 760° C. In any event, conditions and equipment should be selected to obtain small spherical particles; the particles preferably should have an average diameter of less than about 1.0 mm, more preferably from about 0.2 to 0.8 mm, and optimally from about 0.3 to 0.8 mm.

The aluminum-phosphate binder generally is amorphous, i.e., the binder material is essentially of amorphous character. Preferably less than about 10 mass-% of the binder pore volume is micropore volume, characteristic of crystalline material, and the micropore volume more preferably is less than 5% and optimally less than 2% of the pore volume. Crystalline aluminophosphate generally is unsuitable binder material for preparing a strong, crush-resistant catalyst. Material that is not in an amorphous phase generally is present as gamma-alumina; as the phosphorus content of amorphous aluminum phosphate is decreased, therefore, the proportion of gamma-alumina crystalline material is increased. The average bulk density of the spheres also varies with the phosphorus content, as a higher proportion of phosphorus decreases the average bulk density. Surface area also is controlled by phosphorus content: gamma-alumina oil-dropped spherical particles typically have surface areas up to about 250 $m^2/g$, while spheroidal particles of aluminum phosphate may have surface areas of up to about 450 m²/g. Al/P atomic ratios of the binder/matrix generally range from about 1/10 to 100/1, more typically from about 1/5 to 20/1, and often between about 1:1 and 5:1.

The aluminum phosphate binder/matrix also may contain lesser proportions of other inorganic oxides including, but not limited to, magnesia, beryllia, boria, silica, germania, tin oxide, zinc oxide, titania, zirconia, vanadia, iron oxide, chromia, cobalt oxide and the like which can be added to the hydrosol prior to dropping.

It is within the scope of the invention that the catalyst contains a metal component, preferably selected from components of the group consisting of gallium, rhenium and bismuth. Preferably, however, the catalyst consists essentially of a zeolitic aluminosilicate having a pore diameter of from about 5 to 8 Å and an amorphous aluminum phosphate binder.

Optionally, the catalyst may be subjected to precoking in order to increase the proportion of paraxylene in the $C_8$ aromatics product. Precoking of the present catalyst effects a proportion of paraxylene in the product above equilibrium levels at disproportionation conditions, preferably at least about 80 mass-% and optimally about 90 mass-% or more of the $C_8$ aromatics. Precoking is effected on fresh or regenerated catalyst prior to its use for disproportionation at precoking conditions comprising usually at one or more of a higher temperature, lower space velocity, and lower hydrogen-to-hydrocarbon ratio relative to the disproportionation conditions Such operating conditions generally are within the ranges of those disclosed before for disproportionation, with operating temperature being higher and preferably being at least about 50° C. higher than the disproportionation temperature. Precoking time ranges from about 0.5 hours to 10 days. Precoking effects a catalyst coke or carbon content of between about 5 and 40 mass-% carbon, and preferably between about 10 and 30 mass-% carbon. A coke-forming feed for precoking may comprise the feedstock as described herein, or other specific hydrocarbons or mixtures preferably comprising aromatics may be used. Further details relative to precoking are disclosed in U.S. Pat. No. 4,097,543, incorporated herein by reference.

EXAMPLES

The following examples are presented to demonstrate the present invention and to illustrate certain specific embodiments thereof. These examples should not be construed to limit the scope of the invention as set forth in the claims. There are many possible other variations, as those of ordinary skill in the art will recognize, which are within the spirit of the invention.

Example I

An aluminum-phosphate-bound MFI catalyst was prepared to illustrate the disproportionation process of the invention. A first solution was prepared by adding phosphoric acid to an aqueous solution of hexamethylenetetraamine (HMT) in an amount to yield a phosphorus content of the finished catalyst equal to about 3.8 mass-% and a alumina:phosphorus atomic ratio in the binder of about 2:1. A second solution was prepared by adding an ammonia-exchanged MFI-type zeolite having an $Si/Al_2$ ratio of about 39 to enough alumina sol, prepared by digesting metallic aluminum in hydrochloric acid, to yield a zeolite content in the finished catalyst equal to about 70 mass-%. These two solutions were commingled to achieve a homogeneous admixture of HMT, phosphorus, alumina sol, and zeolite. This admixture was dispersed as droplets into an oil bath maintained at about 93° C. The droplets remained in the oil bath until they set and formed hydrogel spheres having a diameter of about 1.6 mm. The spheres were removed from the oil bath, water washed, air dried, and calcined at a temperature of about 650° C. This disproportionation catalyst, utilized to illustrate the process of the invention, was designated Catalyst A.

Example II

Two pilot-plant tests were performed to determine the performance of Catalyst A in a disproportionation process. The tests are designated respectively A and A'.

In Test A, the catalyst was precoked over a period of 34 hours to provide a carbon content sufficient to control activity and selectivity. The precoking was effected at 560° C. and 4 weight hourly space velocity (WHSV) in the presence of nitrogen and at a 0.5:1 hydrogen:hydrocarbon mole ratio.

Disproportionation of pure toluene then was carried out at 2.45 Mpa and 4 WHSV in the presence of pure hydrogen at variable temperatures of 455°, 445° and 435° C. A temperature of about 440° C. was required for 30% toluene conversion. FIG. 1 shows toluene conversion and selectivity to paraxylene (paraxylene/total xylenes) as a function of run length for Test A.

Test A' was carried out in a similar manner to Test A. The catalyst was precoked over a period of 26 hours to provide a carbon content sufficient to control activity and selectivity. The precoking was effected at 562° C. and 4 weight hourly space velocity (WHSV) in the presence of nitrogen and at a 0.5:1 hydrogen:hydrocarbon mole ratio.

Disproportionation of pure toluene then was carried out at 2.45 Mpa and 4 WHSV in the presence of pure hydrogen at variable temperatures of 455°, 416° and 406° C. A temperature of about 416° C. was required for 30% toluene conversion.

Example III

An alumina-bound MFI catalyst was prepared as a reference for contrasting results with the disproportionation process of the invention. Hexamethylenetetraamine (HMT) was added to a solution prepared by adding an ammonia-exchanged MFI-type zeolite having an $Si/Al_2$ ratio of about 39 to enough alumina sol, effected by digesting metallic aluminum in hydrochloric acid, to yield a zeolite content in the finished catalyst equal to about 70 mass-%. The components were commingled to achieve a homogeneous admixture of HMT, alumina sol, and zeolite. This admixture was dispersed as droplets into an oil bath maintained at about 93° C. The droplets remained in the oil bath until they set and formed hydrogel spheres having a diameter of about 1.6 mm. The spheres were removed from the oil bath, water washed, air dried, and calcined at a temperature of about 650° C. This reference catalyst is designated Catalyst X.

Example IV

A pilot-plant test was performed to determine the performance of Catalyst X in a disproportionation reaction using a procedure generally as described in Test A.

The catalyst was precoked over a period of 34 hours to provide a carbon content sufficient to control activity and selectivity. The precoking was effected at 562° C. and 4 weight hourly space velocity (WHSV) in the presence of nitrogen and at a 0.5:1 hydrogen:hydrocarbon mole ratio.

Disproportionation of pure toluene then was carried out at 2.45 Mpa and 4 WHSV in the presence of pure hydrogen at variable temperatures of 457°, 439°, 441° and 431° C. In this Test X, temperature of about 440° C. was required for 30% toluene conversion.

Example V

An extruded alumina-bound MFI catalyst was prepared as a second reference for contrasting results with the disproportionation process of the invention. An ammonia-exchanged MFI-type zeolite and alumina powder were peptized with nitric acid to yield an extrudable dough comprising a ratio of zeolite to alumina of about 70:30 on a dry basis. The dough was extruded to form cylindrical extrudates having a diameter of about 1.6 mm, which were dried and calcined at about 650° C. This reference catalyst is designated Catalyst Y.

Example VI

A pilot-plant test was performed to determine the performance of Catalyst Y in a disproportionation reaction using a procedure generally as described in Test A.

The catalyst was precoked over a period of 42 hours to provide a carbon content sufficient to control activity and selectivity. The precoking was effected at 560° C. and 4 weight hourly space velocity (WHSV) in the presence of nitrogen and at a 0.5:1 hydrogen:hydrocarbon mole ratio.

Disproportionation of pure toluene then was carried out at 2.45 Mpa and 4 WHSV in the presence of pure hydrogen at variable temperatures of 455°, 445° and 435° C. In this Test Y, temperature of about 445° C. was required for 30% toluene conversion.

Example VII

Two extruded alumina-bound MFI catalysts were prepared in the manner of Catalyst Y, crushed and screened to a particle size of 20–40 mesh (0.4–0.8 mm) in order to illustrate the effect of particle size on disproportionation performance. These two catalysts are designated Catalysts Z and Z'.

Precoking of Catalysts Z and Z' was carried out in a manner as described in the previous examples, except that the precoking temperature was about 580° C. and the WHSV was 6.5.

Disproportionation of pure toluene using Catalyst Z' was carried out at 2.45 Mpa and 4 WHSV in the presence of pure hydrogen at variable temperatures of 455° and 440°. In this Test Z, a temperature of about 455° C. was required for 30% toluene conversion.

Disproportionation of pure toluene using Catalyst Z' then was carried out at 2.45 Mpa and 4 WHSV in the presence of pure hydrogen at variable temperatures of 455°, 440°, 425° and 420° C. In this Test Z', temperature of about 425° C. was required for 30% toluene conversion.

Example VIII

Figure 2:
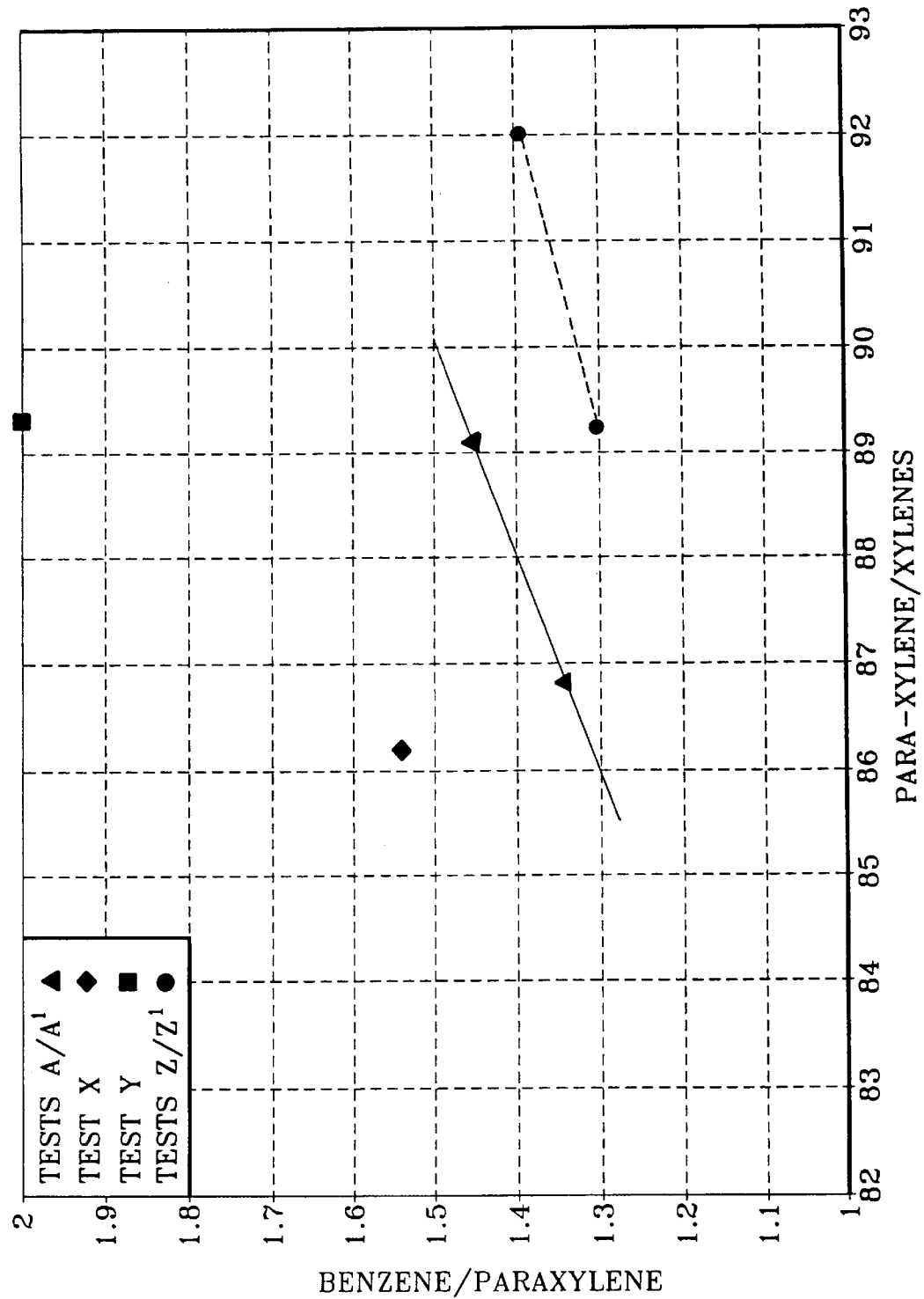
FIG. 2 shows selectivity as benzene/xylenes ratio relative to paraxylene/total xylenes in the product.

A plot of disproportionation results as the ratio of benzene/total xylenes produced vs. the ratio of paraxylene/total xylenes is a meaningful indication of catalyst selectivity. Benzene produced above the stoichiometric 1:1 ratio represents loss of xylenes through removal of sidechains from the aromatic ring. FIG. 2 is a plot of these parameters at 30% toluene conversion for the tests described in the above examples.

Tests A and A' showed a clear advantage for the process and catalysts of the invention relative to reference Tests X and Y. Tests Z and Z' indicated a strong advantage for smaller catalyst particles.

Example IX

Figure 3:
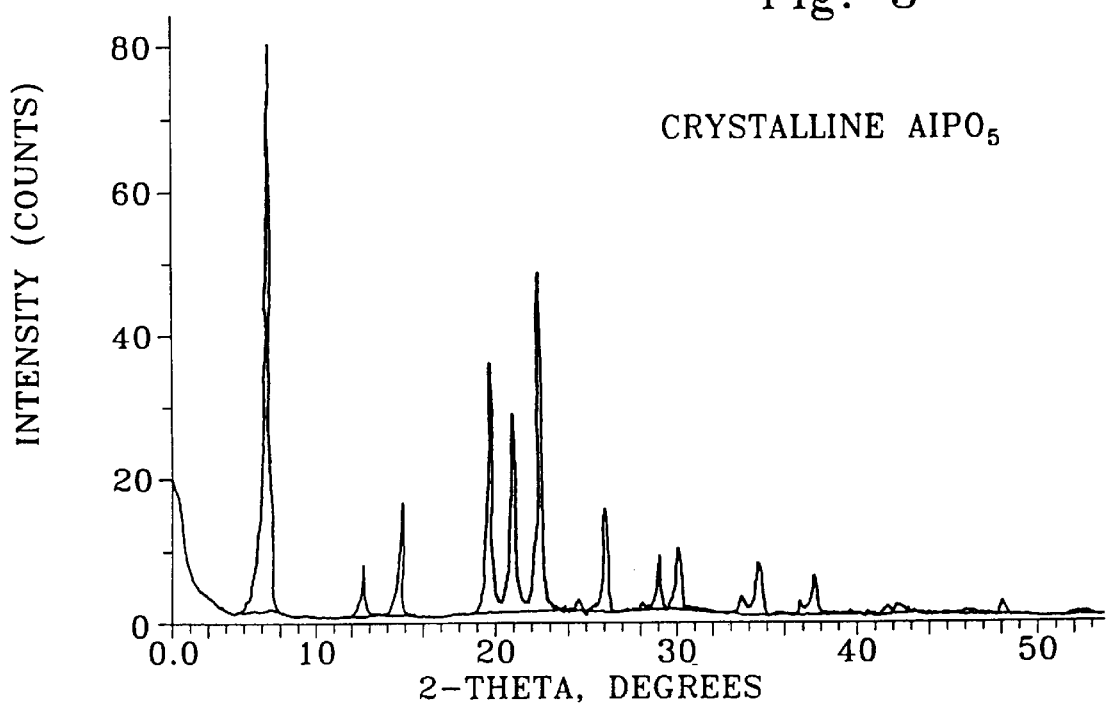
FIG. 3 shows x-ray diffraction patterns for microporous crystalline aluminophosphate and the amorphous aluminum phosphate of the invention.
Figure 3:
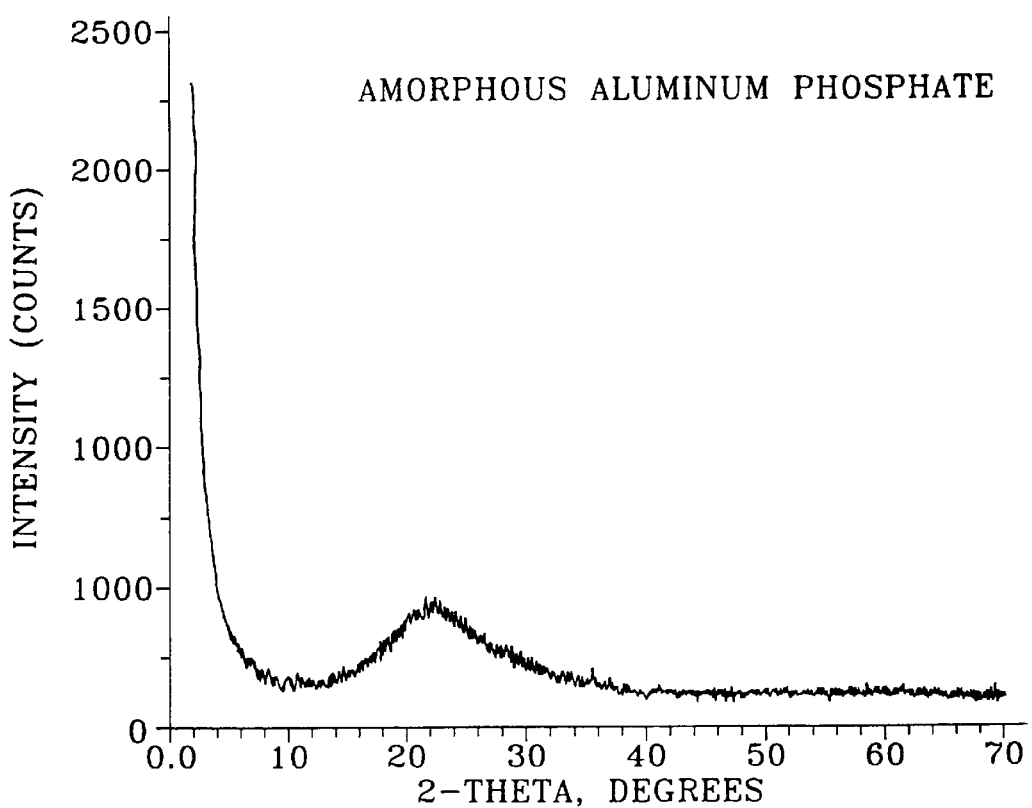

The properties of a microporous crystalline aluminophosphate of the art were contrasted with those of the amorphous aluminum phosphate of the invention. Crystalline material is suitably defined by an x-ray diffraction pattern consisting of sharp peaks at specific diffraction angles relative to the direction of the x-ray beam. A simple x-ray pattern was obtained of powdered AlPO-5, as disclosed in the Kirker et al. U.S. Pat. No. 4,724,066 reference described hereinabove. This is contrasted with that of the amorphous aluminum phosphate of the catalyst used in the present process in FIG. 3. The sharp x-ray diffraction peaks of the crystalline material are in sharp contrast to the weak and very broad peaks of poorly defined diffraction angle of the amorphous aluminum phosphate.

Example X

Microporous crystalline material also is characterized by pore size using various adsorption techniques, such as nitrogen adsorption via the BET technique. A microporous material shows at least a majority of its surface area and pore volume in pores of less than about 2.0 nm, and preferably less that about 1.0 nm. Nitrogen adsorption data on a typical AlPO-5 sample as described above and an amorphous aluminum phosphate sample showed the following:

|  | AlPO-5 | Amorphous |
|---|---|---|
| Micropore area, m$^2$/g | 260.7 | 23.1 |
| Total surface area, m$^2$/g | 320.9 | 197.6 |
| Micropore volume, cc/g | 0.135 | 0.01 |
| Total pore volume, cc/g | 0.222 | 0.873 |

The crystalline material shows well over half of its surface area and pore volume as micropores, while the amorphous aluminum phosphate has less than 15% of its surface area as micropore surface area and just over 1% of its pore volume as micropore volume.

Example XI

An attempt was made to prepare a catalyst by coating MFI zeolite with aluminum phosphate sol by spray-drying, mixing the result with additional aluminum phosphate sol and oil-dropping the composite to form spherical gel particles containing about 70 mass-% MFI zeolite and 30 mass-% aluminum phosphate binder (dry basis). The particles then were subjected to a standard gel-aging step, but disintegrated during the step. Examination of the residue by scanning electron microscope showed that the mixture contained, along with the MFI zeolite, a microcrystalline material having particles approximately 1/20 the size of the zeolite crystals which apparently had been formed from the aluminum phosphate binder. Subsequent analysis of the particles by x-ray diffraction confirmed them to be a crystalline form of AlPO$_4$.

The result of this unsuccessful preparation indicates the unsuitability of crystalline aluminophosphates as binders for the present catalyst due to the physical instability of the formed particles. Such instability has not been observed for preparations in which the aluminum phosphate binder remained in amorphous form.

Example XII

An aluminum-phosphate-bound, surface-silica-enhanced MFI catalyst was prepared to illustrate the disproportionation process of the invention. The MFI component had an Si/Al$_2$ ratio of about 42 and was washed with dilute sulfuric acid before being composited with the binder.

A first solution was prepared by adding phosphoric acid to an aqueous solution of hexamethylenetetraamine (HMT) in an amount to yield a phosphorus content of the finished catalyst equal to about 4.48 mass-% and a alumina:phosphorus atomic ratio in the binder of about 2:1. A second solution was prepared by adding the acid-washed MFI-type zeolite to enough alumina sol, prepared by digesting metallic aluminum in hydrochloric acid, to yield a zeolite content in the finished catalyst equal to about 70 mass-%. These two solutions were commingled to achieve a homogeneous admixture of HMT, phosphorus, alumina sol, and zeolite. This admixture was dispersed as droplets into an oil bath maintained at about 93° C. The droplets remained in the oil bath until they set and formed hydrogel spheres having a diameter of about 1.6 mm. The spheres were removed from the oil bath, water washed, air dried, and calcined at a temperature of about 650° C. This disproportionation catalyst, utilized to illustrate the optional process of the invention, was designated Catalyst B.

Example XIII

A pilot-plant test, designated Test B, was performed to determine the performance of Catalyst B in a disproportionation process.

The catalyst was precoked over a period of 36 hours to provide a carbon content sufficient to control activity and selectivity. The precoking was effected at 562° C. and 4 weight hourly space velocity (WHSV) in the presence of a nitrogen and at a 0.5:1 hydrogen:hydrocarbon mole ratio.

Figure 4:
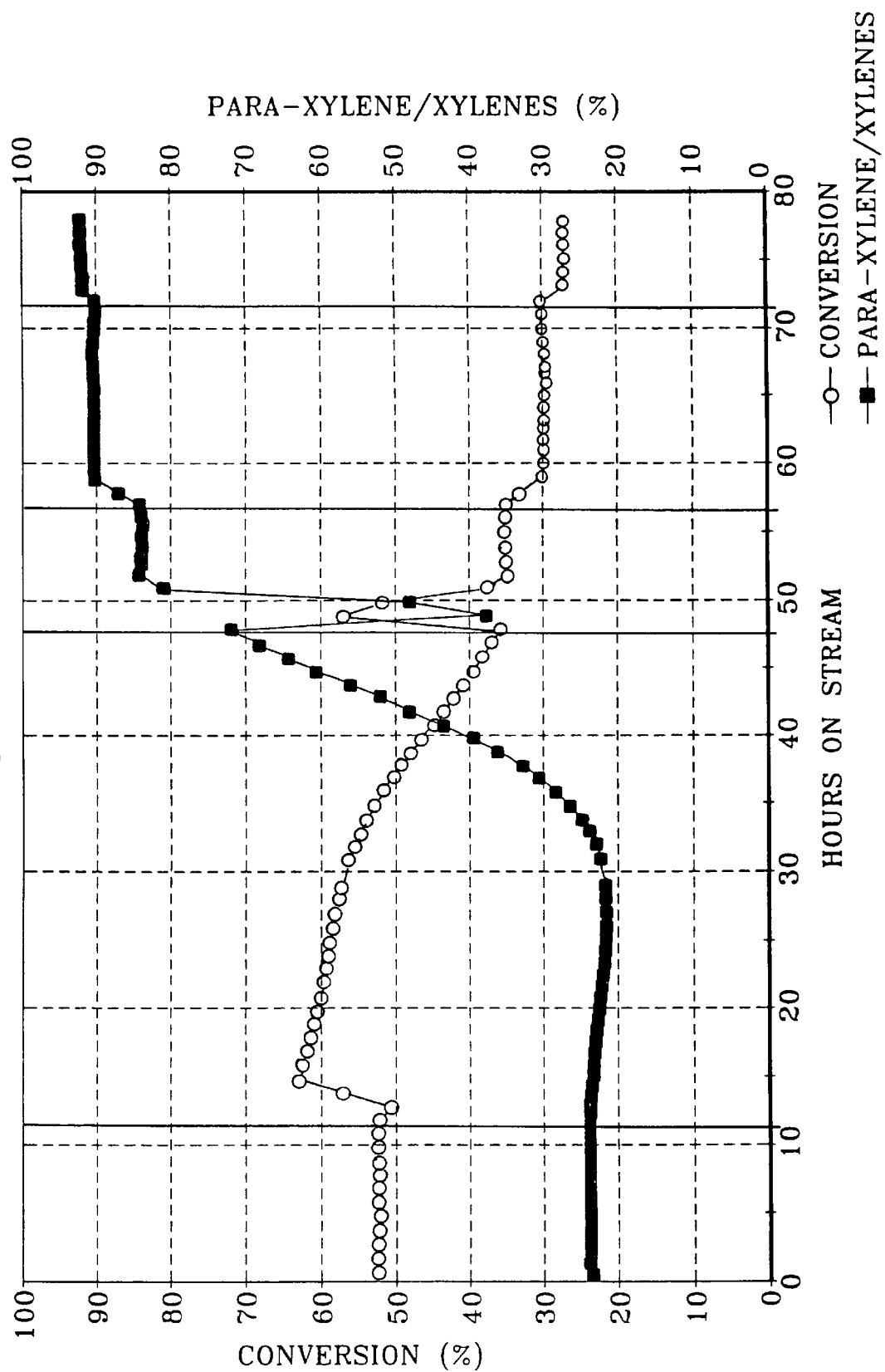
FIG. 4 shows conversion and selectivity in a pilot-plant toluene-disproportionation test using a catalyst having enhanced-surface-silicon MFI.

Disproportionation of pure toluene then was carried out at 2.45 Mpa and 4 WHSV in the presence of pure hydrogen at variable temperatures of 456°, 436° and 427° C. A temperature of about 436° C. was required for 30% toluene (liquid-based) conversion. FIG. 4 shows toluene conversion and selectivity to paraxylene (paraxylene/total xylenes) as a function of run length for Test B.

Example XIV

An aluminum-phosphate-bound MFI catalyst in which the MFI had not been acid-treated or otherwise surface-silica-enhanced was prepared as a control to contrast the disproportionation process of the invention. A first solution was prepared by adding phosphoric acid to an aqueous solution of hexamethylenetetraamine (HMT) in an amount to yield a phosphorus content of the finished catalyst equal to about 6.2 mass-% and a phosphorus:alumina atomic ratio in the binder of about 3/4. A second solution was prepared by adding an ammonia-exchanged MFI-type zeolite having an Si/Al$_2$ ratio of about 43 to enough alumina sol, prepared by digesting metallic aluminum in hydro-chloric acid, to yield a zeolite content in the finished catalyst of about 67 mass-%. The components were commingled to achieve a homogeneous admixture of HMT, alumina sol, and zeolite. This admixture was dispersed as droplets into an oil bath maintained at about 93° C. The droplets remained in the oil bath until they set and formed hydrogel spheres having a diameter of about 1.6 mm. The spheres were removed from the oil bath, water washed, air dried, and calcined at a temperature of about 650° C. This control catalyst was designated Catalyst C.

Example XV

A pilot-plant test was performed to determine the performance of Catalyst C in a disproportionation reaction using a procedure generally as described in Test A, here designated Test C.

The catalyst was precoked over a period of 40 hours to provide a carbon content sufficient to control activity and selectivity. The precoking was effected at 560° C. and 4 weight hourly space velocity (WHSV) in the presence of a nitrogen and at a 0.5:1 hydrogen:hydrocarbon mole ratio.

Disproportionation of pure toluene then was carried out at 2.45 Mpa and 4 WHSV in the presence of pure hydrogen at variable temperatures of 455°, 450°, 440° C. In this Test C, a temperature of about 450–455° C. was required for 30% toluene conversion.

Example XVI

Two pilot-plant tests were performed using Catalyst A to develop a graphical relationship of benzene/xylenes to paraxylenes/xylenes in order to compare the performance of Catalyst B to that of Catalyst C. The present tests are designated respectively R and R'.

In Test R, the catalyst was precoked over a period of 34 hours to provide a carbon content sufficient to control activity and selectivity. The precoking was effected at 560° C. and 4 weight hourly space velocity (WHSV) in the presence of a nitrogen and at a 0.5:1 hydrogen:hydrocarbon mole ratio. Disproportionation of pure toluene then was carried out at 2.45 MPa and 4 WHSV in the presence of pure hydrogen at variable temperatures of 455°, 445° and 435° C. A temperature of about 435° C. was required for 30% toluene conversion.

Test R' was carried out in a similar manner to Test R. The catalyst was precoked over a period of 26 hours to provide a carbon content sufficient to control activity and selectivity. The precoking was effected at 562° C. and 4 weight hourly space velocity (WHSV) in the presence of a nitrogen and at a 0.5:1 hydrogen:hydrocarbon mole ratio. Disproportionation of pure toluene then was carried out at 2.45 Mpa and 4 WHSV in the presence of pure hydrogen at variable temperatures of 455°, 416° and 406° C. A temperature of about 416° C. was required for 30% toluene conversion.

Example XVII

Figure 5:
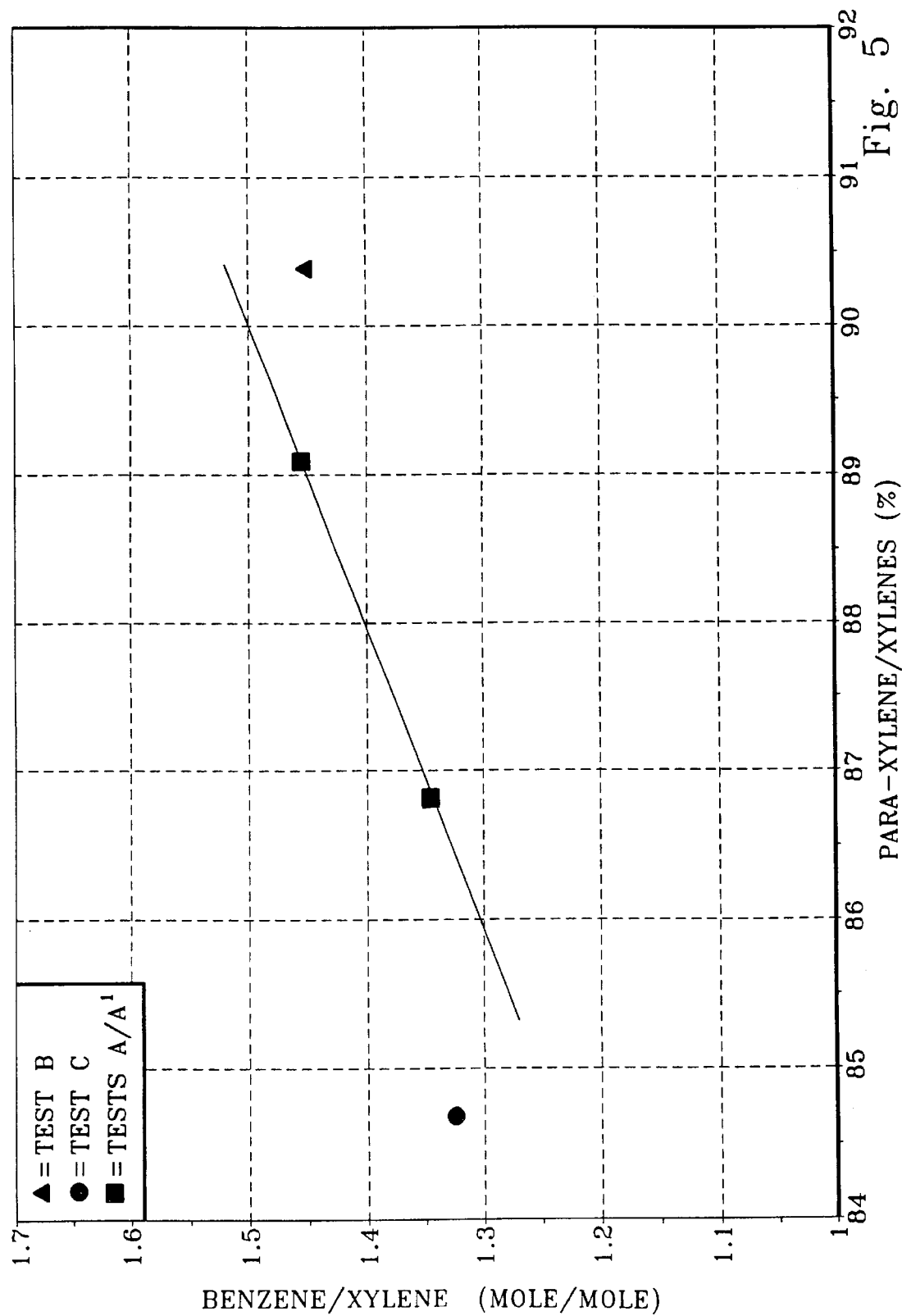
FIG. 5 shows selectivity as benzene/xylenes ratio relative to paraxylene/total xylenes in the product for various catalysts.

A plot of disproportionation results as the ratio of benzene/total xylenes produced vs. the ratio of paraxylene/total xylenes is a meaningful indication of catalyst selectivity. Benzene produced above the stoichiometric 1:1 ratio represents loss of xylenes through dealkylation of the aromatic ring. FIG. 5 is a plot of these parameters at 30% toluene (liquid-based) conversion for the tests described in the above examples.

Tests R and R' used the same catalyst in order to construct a graphical relationship of benzene/xylenes to paraxylene/xylenes in order to compare the performance of Catalyst B to that of Catalyst C Catalyst B of the invention with an enhanced surface silicon content showed a clear advantage, with a low benzene/xylene ratio at over 90% paraxylene/xylenes, relative to the control Catalyst C.

We claim:

1. A process for the disproportionation of toluene in a toluene-containing feedstock, said process comprising contacting the feedstock with a catalyst comprising a substantially phosphorous free zeolitic aluminosilicate having a pore diameter of from about 5 to 8 Å supported in an amorphous aluminum phosphate binder in a disproportionation zone at disproportionation conditions to obtain a paraxylene-containing product.

2. The process of claim 1 further characterized in that the binder has an Al to P atomic ratio of 1:1 to 5:1.

3. The process of claim 2 wherein free hydrogen is present in a molar ratio to feedstock hydrocarbons of about 0.5 to 10.

4. The process of claim 1 wherein the zeolitic aluminosilicate comprises a pentasil zeolite selected from the group consisting of MFI, MEL, MTW and TON.

5. The process of claim 4 wherein the zeolitic aluminosilicate comprises MFI zeolite.

6. The process of claim 1 wherein the disproportionation conditions comprise a temperature of from about 200° to 600° C., a pressure of from about 100 kPa to 6 MPa absolute, and a liquid hourly space velocity of from about 0.2 to 10 $hr^{-1}$.

7. The process of claim 1 further comprising deposition of between about 5 and 40 mass-% carbon on the catalyst prior to its use for disproportionation of the feedstock.

8. The process of claim 1 wherein the product contains paraxylene in excess of its equilibrium concentration at disproportionation conditions.

9. The process of claim 8 wherein the proportion of paraxylene to total xylenes in the paraxylene-containing product is at least about 80 mass-%.

10. A process for the production of paraxylene comprising the steps of:

(a) selectively precoking an oil-dropped spherical catalyst comprising a substantially phosphorous free MFI zeolite and an amorphous aluminum phosphate binder having an Al to P atomic ratio from 1:1 to 5:1 by contacting the catalyst with a coke-forming feed at precoking conditions to deposit between about 5 and 40 mass-% carbon on the catalyst to obtain a selectively precoked catalyst; and, (b) disproportionating a toluene-containing feedstock comprising contacting the feedstock with the selectively precoked catalyst in a disproportionation zone at disproportionation conditions to obtain a paraxylene-containing product containing paraxylene in excess of its equilibrium concentration at disproportionation conditions.

11. A process for the disproportionation of a toluene-containing is feedstock comprising contacting the feedstock with a catalyst comprising a substantially phosphorous free zeolitic aluminosilicate, having a pore diameter of from about 5 to 8 Å and an amorphous aluminum phosphate binder having an Al to P atomic ratio of 1:1 to 5:1 in a disproportionation zone at disproportionation conditions to obtain a paraxylene-containing product, and recovering paraxylene by a series of steps comprising adsorptive separation.

12. The process of claim 11 wherein the paraxylene is recovered by a series of steps which also includes crystallization.

13. The process of claim 11 wherein the recovered paraxylene is oxidized to terphthalic acid and reacted with a glycol to form a polyester which is recovered from the process as a product.

\* \* \* \* \*